United States Patent [19]

Fasnacht

[11] Patent Number: 4,690,787

[45] Date of Patent: Sep. 1, 1987

[54] APPARATUS AND METHOD FOR MAKING POSITIONERS

[76] Inventor: Jeffery L. Fasnacht, 4956 Douglas Ave., Racine, Wis. 53402

[21] Appl. No.: 861,441

[22] Filed: May 9, 1986

[51] Int. Cl.[4] .................... B29C 43/04; B29C 43/52
[52] U.S. Cl. ................................ 264/16; 264/293; 264/320; 425/385; 425/394; 425/397; 425/400; 425/411; 425/445
[58] Field of Search ............... 425/388, 398, 387.1, 425/383, 394, 397, 340, 384, 400, DIG. 13, 406, 407, 411, 412, 445; 264/16, 320, 322, 239, 293, 319; 249/54, 78; 433/5, 6, 18, 74, 54

[56] References Cited

U.S. PATENT DOCUMENTS

| | | |
|---|---|---|
| 714,938 | 12/1902 | McClelland ................ 425/396 |
| 2,467,432 | 4/1949 | Kesling ........................ 433/6 |
| 2,531,222 | 11/1950 | Kesling ........................ 433/6 |
| 2,532,501 | 12/1950 | Johnson ...................... 425/394 |
| 2,775,036 | 12/1956 | Kesling ........................ 433/6 |
| 3,316,640 | 5/1967 | Kesling ........................ 433/6 |
| 3,407,500 | 10/1966 | Kesling ........................ 433/6 |
| 3,429,045 | 2/1969 | Anderson et al. ............ 433/6 |
| 3,510,946 | 5/1970 | Kesling ........................ 433/6 |
| 3,584,109 | 6/1971 | Meadors et al. ............ 425/398 |
| 4,055,895 | 11/1977 | Huge ............................ 433/6 |
| 4,073,061 | 2/1978 | Bergerson ................... 433/6 |
| 4,184,129 | 1/1980 | Gordon ....................... 433/6 |
| 4,370,129 | 1/1983 | Huge ............................ 433/6 |
| 4,419,992 | 12/1983 | Chorbajian ................... 433/6 |
| 4,432,716 | 2/1984 | Kiss ............................ 425/383 |
| 4,448,735 | 5/1984 | Huge ............................ 264/16 |
| 4,504,225 | 3/1985 | Yoshii ......................... 433/6 |
| 4,505,673 | 3/1985 | Yoshii ......................... 433/6 |

*Primary Examiner*—Willard E. Hoag
*Attorney, Agent, or Firm*—Peter N. Jansson

[57] ABSTRACT

Method and apparatus for forming tooth positioners. The apparatus includes a pair of aligned model mounts which are relatively movable toward each other, a holding member between the mounts having a cavity for a positioner blank, a heating element embedded in the holding member, and a sandwiching pressure applicator. Preferred embodiments include a carrier member with which the holding member is removably engageable. The method includes heating the holding member by applying heat internally to it and applying sandwiching pressure to the blank, preferably concurrently.

18 Claims, 4 Drawing Figures

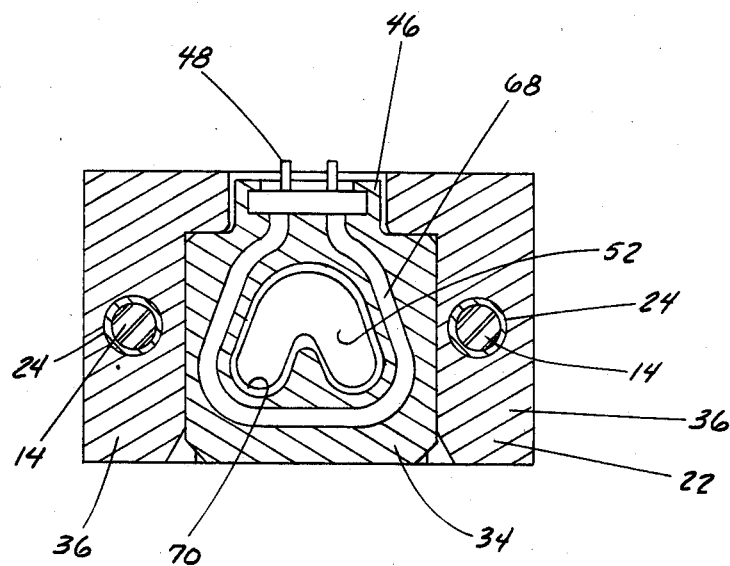
FIG. 3
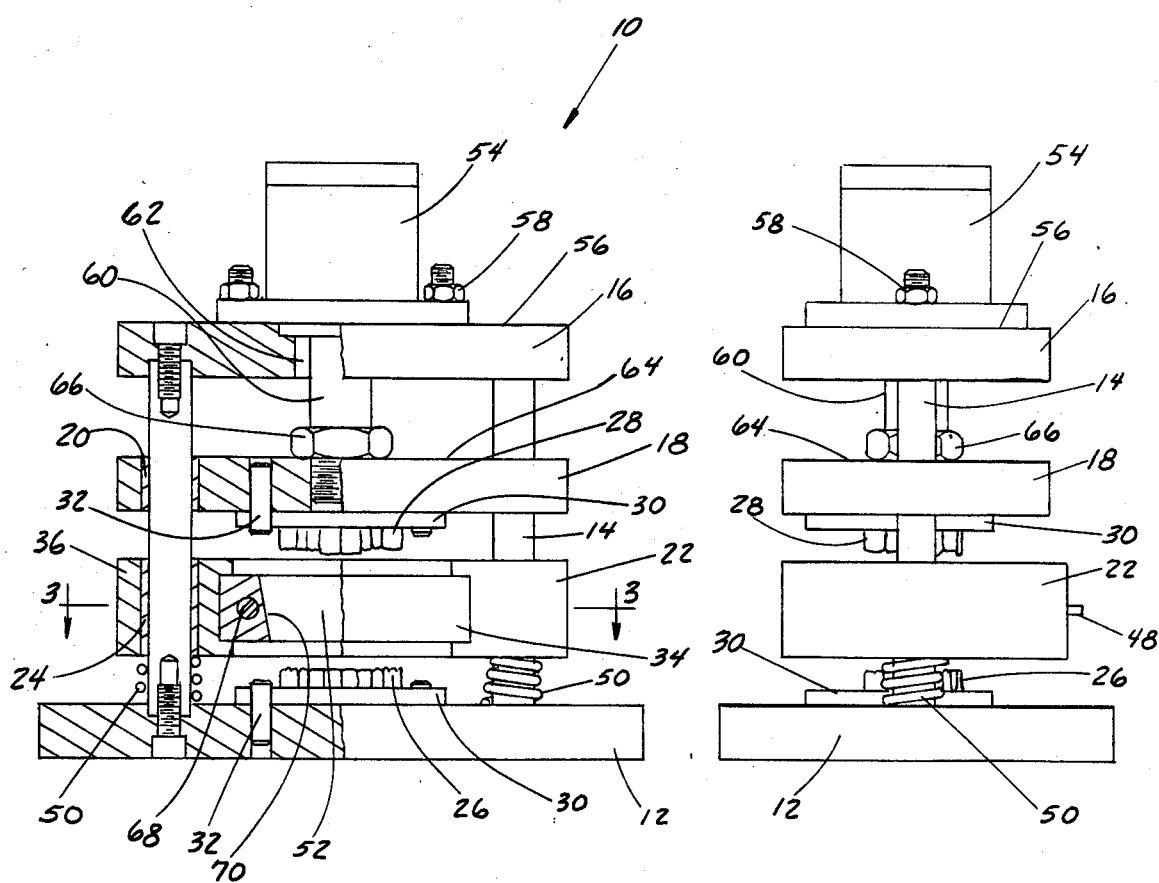
FIG. 2.
FIG. 4

APPARATUS AND METHOD FOR MAKING POSITIONERS

FIELD OF THE INVENTION

This invention is related generally to apparatus and methods for forming dental appliances and, more specifically, to apparatus and methods for the manufacture of orthodontic tooth positioners.

BACKGROUND OF THE INVENTION

Tooth psoitioners are devices which are adapted to surround the teeth of the wearer to support the teeth and adjacent arch forms and/or to direct the teeth and arch forms toward the assumption of preselected ideal positions. Tooth positioners are often generally U-shaped polymeric pieces having negative dental impressions on their upper and lower surfaces.

Such devices have been made in a number of ways. Nearly every positioner-forming method involves exposing a polymeric material (in some form) against toothwork models representing the upper and lower teeth. Typically, the methods involve the application of heat in some fashion and often the application of pressure as well.

During the last fifty years, a number of significant advances have been made in the field of orthodontic appliances, including advances in the manufacture of tooth positioners. A number of United States patents have been granted which disclose various devices and methods for production of orthodontic tooth positioners. Included among these are:

U.S. Pat. Nos. 2,531,222 (H.D. Kesling);
2,775,036 (H.D. Kesling);
3,316,640 (P.C. Kesling);
3,407,500 (P.C. Kesling);
3,429,045 (Anderson et al.);
3,510,946 (P.C. Kesling);
4,055,895 (Huge)
4,073,061 (Bergersen);
4,184,129 (Gordon);
4,370,129 (Huge);
4,419,992 (Chorbajian);
4,448,735 (Huge);
4,504,225 (Yoshii);
4,505,673 (Yoshii).

Despite the advances in the art, it is recognized that there are significant practical problems inherent in existing positioner manufacturing methods. More specifically, the heating and forming steps of many prior methods are very slow, requiring a number of manipulative steps and often requiring equipment which is complex and expensive.

As a result, positioner manufacturing is typically a multi-step procedure, often involving steps at several sites and often resulting in a turn-around time which is medically disadvantageous.

There is a clear need for an improved positioner manufacturing method and apparatus overcoming such problems. More specifically, there is a need for an improved apparatus and method which will make is possible for local laboratories, which can meet the requirements of a limited group of nearby orthodontists, to manufacture tooth positioners without making large capital investments. There is a need for a tooth positioner manufacturing method and apparatus which will reduce the turn-around time and thus improve the practice of orthodontic dentistry.

SUMMARY OF THE INVENTION

This invention is an improved apparatus and an improved method for forming tooth positioners. The apparatus and method of this invention overcome the aforementioned problems and disadvantages.

The apparatus of this invention includes a pair of aligned, opposed toothwork model mounting means which are movable relatively toward each other, a holding member between the mounting means having a cacity to receive a positioner blank, a heating means embedded in the holding member itself, adjacent to the cavity, and means to apply sandwiching pressure onto a blank in the cavity through the mounting means and the toothwork models which are on them.

The apparatus of this invention allows the specific application of heat to the blank during the application of the sandwiching pressure, and may be in a compact, inexpensive, and easily-operatable form.

In preferred embodiments, the heating means embedded in the holding member surrounds the cavity. The most preferred heating means is an electric heating element.

In preferred embodiments, the holding member is removably mountable in a carrier member which is secured in alignment with the opposed toothwork model mounting means. The carrier member preferably has side portions with opposed slots or other slide means, and a back portion joined to the side portions. The holding member has edges which are slideably engagable with such slots or other slide means. This facilitates removal and replacement of the holding member from the apparatus.

In a preferred embodiment, the holding member has a rear edge with an electrical connector extending from it, and the back portion of the carrier member includes an opening for receiving the electrical connector. This facilitates electrical connection of the heating element at the rear of the apparatus.

In a highly preferred form, the apparatus of this invention includes a fixed toothwork model mounting means and a movable toothwork model mounting means. For example, the mount for the lower toothwork model may be fixed while the mount for the upper toothwork model may be movable. The mounting means are preferably metal plates.

Guide means, such as parallel vertical rods, extend from the fixed mounting means upwardly to a fixed end member, and the movable mounting means and carrier member are slideably engaged on the rods or other guide means. The pressure-applying means is mounted on the fixed end member and has a pusher element, such as a piston rod, extending to the movable mounting means. A pneumatic cylinder is a highly preferred pressure-applying means.

The carrier means is biased by springs or other biasing means, which extend between the fixed mounting means and the carrier member, such that a blank within the cavity of the holding member (which is carried by the carrier member is removed from contact with the toothwork model on the fixed mounting means except when sandwiching pressure is applied.

During the application of sandwiching pressure, the movable mounting means is pushed by the pressure-applying means such that the toothwork model thereon engages one side of the positioner blank. Such pressure pushes the blank, which in turn pushes the carrier member, against the biasing pressure of the springs or other biasing means, until the toothwork model on the fixed mounting means engage the opposite side of the blank. As additional pressure is applied, it is applied to the blank as sandwiching pressure allowing formation of both the upper and lower surfaces of the positioner. Such sandwiching pressure is effective in quickly forming the positioner when heat has been applied to the blank by means of the internal application of heat to the holding member, as previously described.

The improved method of this invention includes aligning a pair of upper and lower toothwork models, loading a positioner blank into a blank-receiving cavity of a holding member, placing such loaded holding member between the upper and lower toothwork models in alignment therewith, heating the loaded holding member by applying heat internally to the holding member, and applying sandwiching pressure to the blank through the toothwork models. The only application of heat which is required is the heat internally applied to the holding member.

In a preferred form, the placing of the loaded holding member is accomplished by engaging the holding member with a carrier member permanently aligned with respect to mounting means for the upper and lower toothwork models.

It is highly preferred that the application of heat and sandwiching pressure be concurrent. That is, while pressure is applied, heat is being applied internally to the holding member. Concurrent means at least overlapping. The heating step can begin prior to the application of pressure and can end prior to termination of the pressure. It is preferred that the application of pressure and heat begin and end at about the same time.

It is highly preferred that the material used for the positioner blanks be a polyurethane elastoplastic polymer. A particularly preferred materials are the dentally-acceptable polymers sold under the trademark Pellethane by the UpJohn Company of Farmington Hills, Michigan. A variety of other polymeric materials are acceptable.

OBJECTS OF THE INVENTION

It is an object of this invention to provide an improved tooth positioner manufacturing apparatus and method overcoming some of the problems and deficiencies of the prior art.

Another object of this invention is to provide an improved apparatus for forming tooth positioners which reduces the turnaround time in positioner manufacturing.

Another object of this invention is to provide a method and apparatus for forming tooth positioners which minimizes the manipulative steps in the manufacturing process.

Another object of this invention is to provide an improved apparatus and method for forming tooth positioners which is easy to use and involves a reduced capital investment.

These and other objects will be apparent from the following additional descriptions and from the drawings, wherein:

BRIEF DESCRIPTION OF THE DRAWINGS

FIG. 2 is a partially sectional front elevation.

FIG. 3 is a sectional view (without background) taken along section 3—3, as indicated in FIG. 2.

FIG. 4 is a right side elevation of FIG. 2.

DETAILED DESCRIPTIONS OF PREFERRED EMBODIMENTS

Figure 1:
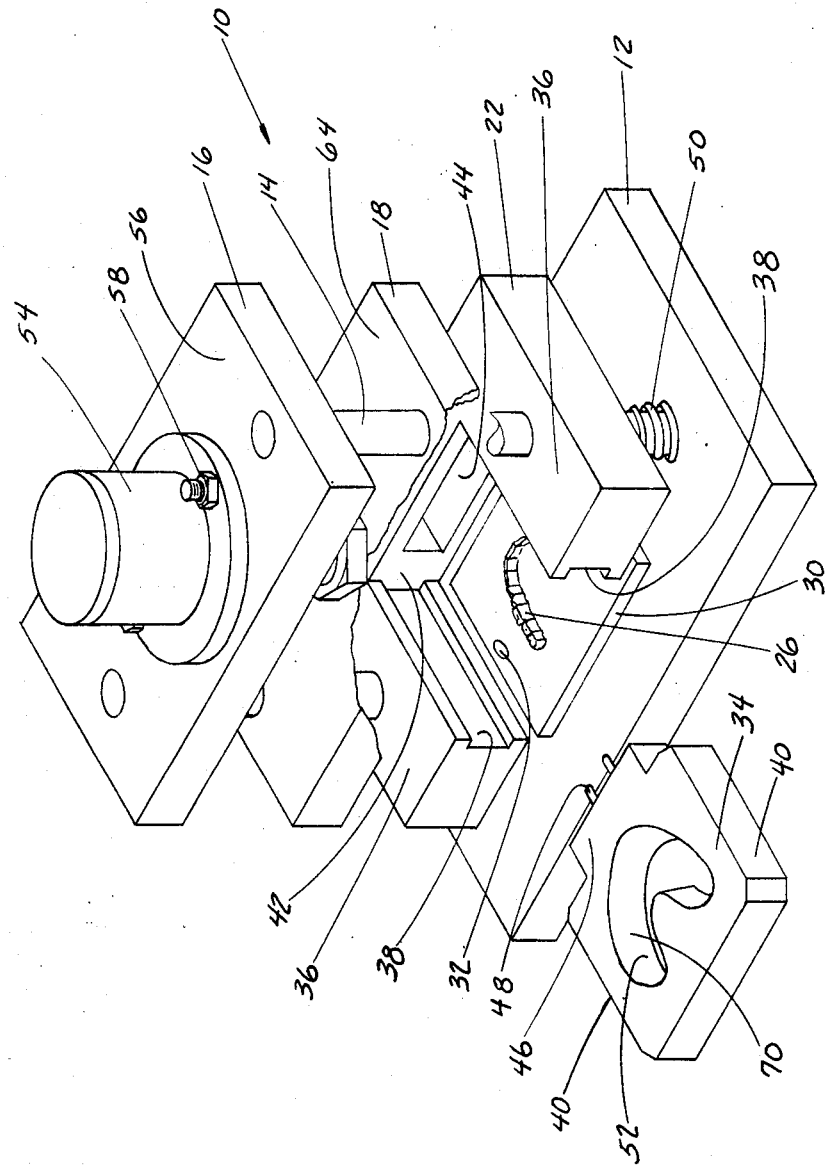
FIG. 1 is a partially cut-away perspective view of a preferred apparatus in accordance with this invention.

The figures illustrate a positioner-forming apparatus 10 which is a preferred embodiment of this invention.

Positioner-forming apparatus 10 has a base member 12, which also functions as a fixed toothwork model mounting plate, a pair of vertical rods 14 secured to base member 12 and extending upwardly, and a fixed end member 16 which is secured at the upper ends of vertical rods 14. Base member 12, vertical rods 14 and fixed end member 16 form a frame with respect to which other elements of positioner-forming apparatus 10 are movably mounted. Vertical rods 14 serve as alignment and guide means for the movable members hereafter described.

A movable toothwork model mounting plate 18 is slideably engaged with vertical rods 14 by means of a pair of holes extending through mounting plate 18. As illustrated in FIG. 2, movable mounting plate 18 includes slide bearings 20 which engage vertical rods 14. Also slideably mounted on vertical rods 14 is a carrier member 22, such mounting also being by means of holes through carrier member 22. As illustrated in FIGS. 2 and 3, carrier member 22 includes slide bearings 24 which engage vertical rods 14.

Fixed model mounting plate 12 and movable mounting plate 18 have opposed lower and upper toothwork models 26 and 28, respectively, secured thereto, in each case by means of a mount 30. The details of mount 30, lower toothwork model 16 and upper toothwork model 28 do not form part of this invention. However, mounts 30 may be secured to mounting plates 12 and 18 by means of connectors 32, shown in FIGS. 1 and 2. Toothwork models 26 and 28 are made of plaster, as is common in the industry.

A holding member 34 is removably engageable with carrier member 22. Carrier member 22 includes side portions 36 each of which has a horizontal slot 38 dimensioned to receive the opposite edges 40 of holding member 34. Slots 38 form opposed slide means which facilitate removable mounting of holding member 34 in carrier member 22.

Carrier member 22 also includes a back portion 42 which is joined to the two side portions 36; indeed, back portion 42 and side portions 36 are integrally formed. Back portion 42 includes a centrally located horizontal opening 44 which is dimensioned to receive a rearwardly extending portion 46 of holding member 34. An electrical plug 48 extends rearwardly from rearwardly extending portion 46 such that, when holding member 34 is fully engaged with carrier member 22, plug 48 is readily accessible behind positioner-forming apparatus 10.

Carrier member 22 is supported by coil springs 50 which extend around vertical rods 14 between fixed model mounting plate 12 and carrier member 22. Springs 50 bias carrier member 22 to a vertical position such that lower toothwork model 26 is clear of holding member 34 except when carrier member 22 is depressed, as will hereafter be explained. FIGS. 1, 2 and 4 illustrate carrier member 22 biased to such clear position.

Holding member 34 includes a cavity 52 which is shaped to receive a positioner blank. When holding member 34 is fully engaged with carrier member 22, a positioner blank within cavity 52 is vertically aligned with lower and upper toothwork models 26 and 28. Such arrangement allows toothwork models 26 and 28 to engage the lower and upper surfaces of a positioner blank, and allows sandwiching pressure to be applied to the blank by such toothwork models.

Such pressure is applied in the following manner: An air cylinder 54 is secured to the top surface 56 is fixed end member 16 by means of bolts 58. Air cylinder 54 includes a piston rod 60 extending through an opening 62 in fixed end member 16. Piston rod 60 is secured to the upper surface 64 of movable mounting plate 18 by means of threaded engagement with it, as illustrated in FIG. 2. Such threaded engagement is adjustable by means of nut 66.

A preferred air cylinder is a Bimba air cylinder having a 1½ inch stroke. However, a variety of other air cylinders or other small mechanical displacement units can be used.

By virtue of the attachment of piston rod 60 to movable mounting plate 18, sandwiching pressure is applied to a positioner blank held within cavity 52 through lower and upper toothwork models 26 and 28. As downward pressure is applied to the positioner blank through piston rod 60, movable model mounting plate 18 and upper toothwork model 28, holding member 34 and its carrier member 22 are depressed. Carrier member 22 transmits the downward loading pressure on coil springs 50 until the lower surface of the positioner blank contacts lower toothwork model 26. As the loading pressure of air cylinder 54 continues, sandwiching pressure is applied to such positioner blank.

Embedded within holding member 34 is an electrical element 68, illustrated best in FIGS. 2 and 3. Electrical element 68 surrounds cavity 52 and applies heat specifically to holding member 34 and thus quite directly to a positioner blank within cavity 52. Heating element 68 is electrically connected to plug 48. When holding member 34 is fully engaged with carrier member 22, a plug 48, which extends through opening 44 in back portion 42 of carrier member 22, may readily be connected to an electrical supply.

Embedded electrical heating element 68 allows the specific application of heat to the blank, thus avoiding the need for ovens or other complex heating or preheating equipment. And, the combination of such a heating system with a pressure-applying means of the type described allows formation of a tooth positioner by means of a readily usable inexpensive apparatus.

In surrounding cavity 52, embedded electrical heating element 68 is located close to the wall 70 of cavity 52 and is substantially equally spaced therefrom around cavity wall 70. This improves the evenness of heat application.

Cavity wall 70 is beveled, as illustrated in FIGS. 2 and 3. This facilitates removal of a formed positioner after heat and sandwiching pressure have been applied.

The method of this invention includes the steps of: aligning lower and upper toothwork models 26 and 28; loading a positioner blank into blank-receiving cavity 52 of holding member 34; placing loaded holding member 34 between lower and upper toothwork models 26 and 28 with the blank in alignment with such models; heating the loaded holding member by applying heat internally to the holding member; and applying sandwiching pressure to the blank through toothwork models 26 and 28.

In preferred forms, the heating and loading steps are concurrent or at least overlapped, as previously noted. That is, sandwiching pressure is applied while heat is being applied internally to holding member 34.

The parts of positioner-forming apparatus 10 may be made of well-known materials. For example, base member 12, vertical rods 14, fixed end member 16, movable toothwork model mounting plate 18, and holding member 34 may all be made of steel, preferably stainless steel, or other hardened materials. The slide bearings are preferably heat-resistant bearings, and may be made of Teflon or other suitable materials. Coil springs 50 and all the connectors are made of common materials.

Holding member 34 or carrier member 22 may include a heat insulating portion which limits the spread of heat from heating element 68 to other portions of apparatus 10. For example, slots 38 may be lined with such insulating material, or such insulating material can be along opposite edges 40 of holding member 34.

As previously noted, a variety of materials can be used for positioner blanks in the method of this invention. The aforementioned polyurethane elastoplastic polymers sold under the trademark Pellethane are particularly preferred.

A number of variations are, of course, possible. Electrical heat may be applied internally to holding member 34 using a variety of heating elements. And, heat may be directed specifically internally to holding member 34 by other means.

While the principles of this invention have been described in connection with specific embodiments, it should be understood clearly that these descriptions are made only by way of example and are not intended to limit the scope of the invention.

What is claimed:

1. In apparatus for forming tooth positioners of the type including a pair of aligned opposed toothwork model mounting means relatively movable toward each other and a holding member between the mounting means having a cavity to receive a positioner blank, the improvement comprising:
    heating means embedded in the holding member; and
    means to apply pressure on upper and lower surfaces of a blank in the cavity through the mounting means and the toothwork models thereon to shape the blank on the upper and lower surfaces,
whereby heat can be specifically applied to the blank.

2. The apparatus of claim 1 wherein the heating means surrounds the cavity.

3. The apparatus of claim 2 wherein the heating means comprises an electric heating element.

4. The apparatus of claim 1 wherein the holding member is removably mountable in a carrier member secured in alignment with both of the mounting means.

5. The apparatus of claim 4 wherein:
    the carrier member comprises side portions having opposed slide means and a back portion joined to the side portions; and
    the holding member has edges slideably engagable with the slide means;
thereby facilitating removal and replacement of the holding member.

6. The apparatus of claim 5 wherein:
    the holding member has a rear edge with an electrical connector extending therefrom; and
    the back portion of the carrier member includes an opening for receiving the electrical connector.

7. The apparatus of claim 4 wherein the pair of mounting means include a fixed mounting means and a movable mounting means, and further comprising:
a fixed end member;
guide means connected to the fixed mounting means and extending therefrom to the fixed end member, the carrier member and the movable mounting means being slideably engaged to the guide means; and
said pressure-applying means being mounted on the fixed end member and having a pusher extending to the movable mounting means.

8. The apparatus of claim 7 wherein the pressure-applying means is a pneumatic cylinder.

9. The apparatus of claim 7 wherein the guide means include a pair of rods extending through the carrier member and the movable mounting means.

10. The apparatus of claim 9 further comprising biasing means between the fixed mounting means and the carrier member to prevent contact of a blank in the carrier member with a toothwork model on the fixed mounting means until pressure is to be applied.

11. The apparatus of claim 10 wherein the heating means surrounds the cavity.

12. The apparatus of claim 11 wherein the heating means comprises an electric heating element.

13. The apparatus of claim 10 wherein:
the carrier member comprises side portions having opposed slide means and a back portion joined to the side portions; and
the holding member has edges slideably engagable with the slide means,
thereby facilitating removal and replacement of the holding member.

14. The apparatus of claim 13 wherein:
the holding member has a rear edge with an electrical connector extending therefrom; and
the back portion of the carrier member includes an opening for receiving the electrical connector.

15. The apparatus of claim 14 wherein electric heating means surrounds the cavity.

16. The apparatus of claim 15 wherein the electric heating means is an elongated heating element.

17. A method for forming tooth positioners comprising:
mounting a pair of upper and lower toothwork models on aligned opposed toothwork model mounting means;
loading a positioner blank into a blank-receiving cavity of a holding member;
placing the loaded holding member between the upper and lower toothwork models with the blank in alignment with the models;
heating the loaded holding member by applying heat internally to the holding member; and
applying pressure simultaneously to upper and lower surfaces of the blank through the toothwork models.

18. The method of claim 17 wherein the heating and pressure-applying steps are concurrent.

* * * * *